US012434000B2

(12) United States Patent
Bosshardt et al.

(10) Patent No.: US 12,434,000 B2
(45) **Date of Patent: *Oct. 7, 2025**

(54) ADAPTOR AND DRUG DELIVERY DEVICE

(71) Applicant: Becton Dickinson France, Le Pont-de-Claix (FR)

(72) Inventors: Michel Bosshardt, Claix (FR); Benoit Guillard, Grenoble (FR)

(73) Assignee: Becton Dickinson France, Le Pont-de-Claix (FR)

( * ) Notice: Subject to any disclaimer, the term of this patent is extended or adjusted under 35 U.S.C. 154(b) by 760 days.

This patent is subject to a terminal disclaimer.

(21) Appl. No.: 17/837,461

(22) Filed: Jun. 10, 2022

(65) Prior Publication Data

US 2022/0296813 A1 Sep. 22, 2022

Related U.S. Application Data

(63) Continuation of application No. 16/509,539, filed on Jul. 12, 2019, now Pat. No. 11,383,039, which is a continuation of application No. 15/634,004, filed on Jun. 27, 2017, now Pat. No. 10,391,248, which is a continuation of application No. 13/994,273, filed as (Continued)

(51) Int. Cl.

*A61M 5/24* (2006.01)
*A61M 5/31* (2006.01)
*A61M 39/10* (2006.01)

(52) U.S. Cl.

CPC ................ *A61M 5/24* (2013.01); *A61M 5/31* (2013.01); *A61M 39/1011* (2013.01); *A61M 2005/2444* (2013.01); *A61M 2039/1027* (2013.01); *A61M 2039/1077* (2013.01)

(58) Field of Classification Search

CPC ...... A61M 5/24; A61M 5/31; A61M 39/1011; A61M 2005/2444; A61M 2039/1027; A61M 2039/1077; A61M 1/86; A61M 39/10; A61M 39/20

See application file for complete search history.

(56) References Cited

U.S. PATENT DOCUMENTS

| | | | |
|---|---|---|---|
| 5,395,348 | A | 3/1995 | Ryan |
| 5,509,911 | A | 4/1996 | Cottone, Sr. et al. |

(Continued)

FOREIGN PATENT DOCUMENTS

| | | | |
|---|---|---|---|
| CN | 1311704 | | 9/2001 |
| DE | 4318101 | A1 | 12/1994 |

(Continued)

*Primary Examiner* — Lauren P Farrar
(74) *Attorney, Agent, or Firm* — The Webb Law Firm

(57) ABSTRACT

An adapter for use with a drug delivery device having a reservoir for containing a product, the reservoir having a distally projecting end-piece defining a passageway for the transfer of the product from the reservoir, includes a collar engageable with the end-piece, an adaptor securing member limiting translational movement of the collar with respect to the end-piece once the collar is engaged with the end-piece, at least one adaptor anti-rotation member limiting the rotation of the collar with respect to the end-piece once the collar is engaged with the end-piece, at least one deactivating member neutralizing the adaptor anti-rotation member in response to a turning torque equal or greater than a predetermined value applied to the collar when the collar is engaged with the end-piece, thereby allowing the rotation of the collar with respect to the end-piece.

20 Claims, 4 Drawing Sheets

Figure 1:
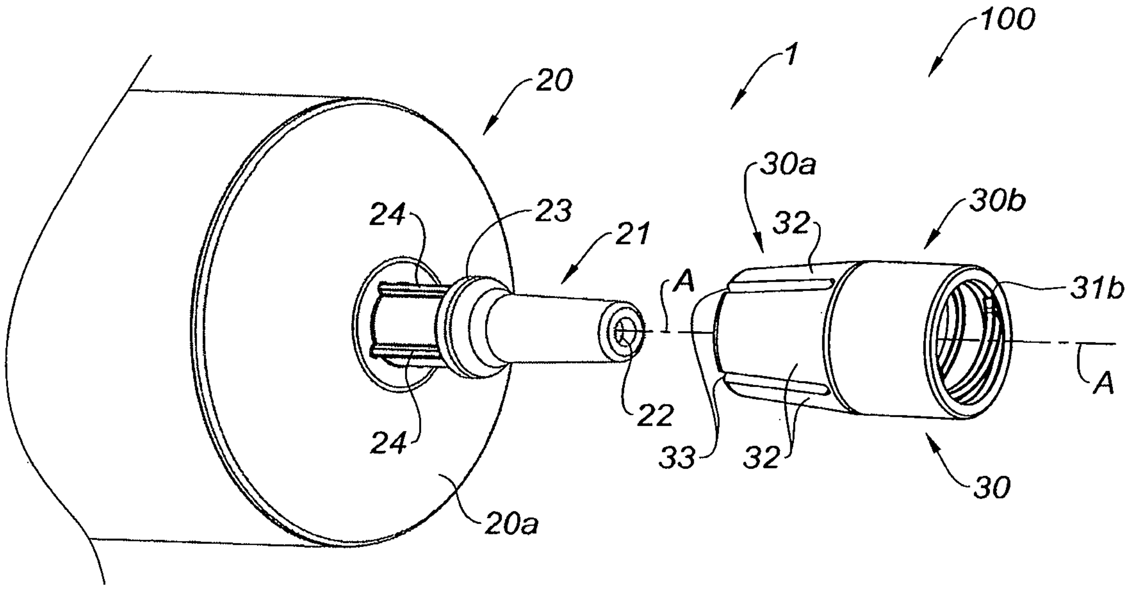

Related U.S. Application Data application No. PCT/IB2010/003493 on Dec. 16, 2010, now Pat. No. 9,717,855.

(56) References Cited

U.S. PATENT DOCUMENTS

| | | | |
|---|---|---|---|
| 5,591,143 | A | 1/1997 | Trombley, III et al. |
| 5,620,427 | A | 4/1997 | Werschmidt et al. |
| 5,693,025 | A | 12/1997 | Stevens |
| 6,152,913 | A | 11/2000 | Feith et al. |
| 6,190,364 | B1 | 2/2001 | Imbert |
| 6,196,998 | B1 | 3/2001 | Jansen et al. |
| 6,520,935 | B1 | 2/2003 | Jansen et al. |
| 7,244,249 | B2 | 7/2007 | Leinsing et al. |
| 2003/0153895 | A1 | 8/2003 | Leinsing |
| 2004/0201216 | A1 | 10/2004 | Segal et al. |
| 2006/0129109 | A1 | 6/2006 | Shaw et al. |
| 2008/0287920 | A1 | 11/2008 | Fangrow et al. |
| 2009/0171322 | A1 | 7/2009 | Kurimoto et al. |
| 2011/0282295 | A1 | 11/2011 | Pupke et al. |
| 2012/0116355 | A1 | 5/2012 | Heinz et al. |
| 2013/0338603 | A1 | 12/2013 | Roedle et al. |

FOREIGN PATENT DOCUMENTS

| | | | |
|---|---|---|---|
| EP | 0633038 | A1 | 1/1995 |
| EP | 0707859 | A1 | 4/1996 |
| EP | 0720857 | A1 | 7/1996 |
| EP | 0812216 | A1 | 12/1997 |
| EP | 0856332 | A1 | 8/1998 |
| EP | 0941743 | A2 | 9/1999 |
| EP | 1080742 | A1 | 3/2001 |
| EP | 1378223 | A1 | 1/2004 |
| EP | 1410817 | A1 | 4/2004 |
| EP | 1410819 | A1 | 4/2004 |
| EP | 1563863 | A1 | 8/2005 |
| EP | 1600190 | A1 | 11/2005 |
| EP | 1658107 | A1 | 5/2006 |
| EP | 1779882 | A2 | 5/2007 |
| EP | 1923086 | A1 | 5/2008 |
| EP | 2051754 | A2 | 4/2009 |
| EP | 2087921 | A1 | 8/2009 |
| EP | 2424600 | A2 | 3/2010 |
| EP | 2253349 | A1 | 11/2010 |
| EP | 2262560 | A1 | 12/2010 |
| GB | 2379253 | A | 3/2003 |
| JP | 3500983 | A | 2/1996 |
| JP | 2005536174 | A | 11/2005 |
| JP | 2007029561 | A | 2/2007 |
| JP | 4156790 | B2 | 9/2008 |
| JP | 2008246070 | A | 10/2008 |
| JP | 4299509 | B2 | 7/2009 |
| JP | 2010233954 | A | 10/2010 |
| WO | 9625964 | A1 | 8/1996 |
| WO | 0139821 | A1 | 6/2001 |
| WO | 02056958 | A2 | 7/2002 |
| WO | 2005023343 | A1 | 3/2005 |
| WO | 2007131086 | A2 | 11/2007 |
| WO | 2007146921 | A2 | 12/2007 |
| WO | 2008010958 | A2 | 1/2008 |
| WO | 2009102624 | A1 | 8/2009 |
| WO | 2009109312 | A1 | 9/2009 |
| WO | 2010034356 | A1 | 4/2010 |
| WO | 2010124676 | A1 | 11/2010 |
| WO | 2014072440 | A1 | 5/2014 |
| WO | 2014086437 | A1 | 6/2014 |
| WO | 2014049097 | A1 | 9/2014 |

ADAPTOR AND DRUG DELIVERY DEVICE

CROSS REFERENCE TO RELATED APPLICATIONS

This application is a continuation of U.S. patent application Ser. No. 16/509,539, filed Jul. 12, 2019, entitled "Adaptor and Drug Delivery Device", which is a continuation of U.S. patent application Ser. No. 15/634,004, filed on Jun. 27, 2017, entitled "Adaptor and Drug Delivery Device" (now U.S. Pat. No. 10,391,248), which is a continuation of U.S. patent application Ser. No. 13/994,273, filed on Dec. 16, 2010, entitled "Adaptor and Drug Delivery Device" (now U.S. Pat. No. 9,717,855), which is a national stage entry of International Application Serial No. PCT/IB2010/003493, filed Dec. 16, 2010, entitled "Adaptor and Drug Delivery Device", the disclosures of each of which are hereby incorporated by reference in their entirety.

The present invention relates to an adaptor for, or intended to be used with, a drug delivery device having an end-piece, the adaptor having a collar engageable around said-piece and enabling the safe connection of a connector on said collar. The invention further relates to a drug delivery device comprising such an engageable adaptor.

Drug delivery devices usually comprise a hollow body forming a reservoir for containing a medical product. In addition, the distal end of the body forming the reservoir usually comprises an end-piece in which an axial passageway is arranged through which the said product is ejected from the reservoir.

In this application, the distal end of a component or of a device must be understood as meaning the end furthest from the hand of the user and the proximal end must be understood as meaning the end closest to the hand of the user. Similarly, in this application, the distal direction must be understood as the direction of injection or transfer of the product (i.e. from the reservoir to the Intra Veinous line) and the proximal direction is the opposite direction.

Moreover, the reservoir and end-piece of a drug delivery device may be made of various materials such as glass or plastic. When it is known that the stability of the product stored in the reservoir is not impacted by the plastic nature of the wall of the reservoir, it is desirable to have a drug delivery device made of plastic materials, so as to avoid the common risks associated with the handling of glass material. Actually, when drug delivery devices made of glass material happen to break, not only the product they may contain is lost, but the resulting bits of glass material constitute danger for the persons who happen to be around. Moreover, the product lost may also generate a danger when such product is for example a toxic drug.

It is also desirable to have drug delivery devices made of plastic materials when these drug delivery devices are prefilled with the product and provided to the final user in a prefilled state: risks of breaking the drug delivery device during the various operations before its use, such as the steps of prefilling, sterilization, packaging, transport, storage, are therefore substantially limited.

The handling of products, such as liquid medicine, in particular for a parenteral administration to a patient which is carried out via a perfusion device, as often in hospitals or in emergency situations, implies, in a general manner, the use of connectors, such as IV (Intra Veinous) connectors which link the drug delivery device, containing the product to be delivered, to the vein of the patient, usually via an IV line. Of course, the drug delivery device, in particular its end-piece and the connector must be assembled together correctly and securely.

In this view, the drug delivery device usually comprises an external collar surrounding the end-piece, this collar being intended to be connected to a connector so as to facilitate the transfer of the product from the end-piece of the drug delivery device to the connector, and then in the IV line.

At the time the connector is connected to the collar, the collar is submitted to a stress resulting from the force applied in order to connect the connector thereon. The intensity of the force applied may vary depending on the way the connector is connected on the collar: generally, the inner wall of the collar is provided with a thread and the connector is connected to the collar by screwing. The intensity of the force applied during the screwing step depends on the user. A first consequence is that the stress to which the collar is submitted to when the connector is connected thereon is not controllable.

Moreover, it happens that the collar surrounding the end-piece of the drug delivery device breaks or cracks at the time it is submitted to the necessary stress for connecting the connector thereon, for example because the user screws the connector within the collar with a too high force and does not stop the screwing in time. In such a case, the connector is not securely and correctly connected to the end-piece of the drug delivery device, and the administration of the medicine is made impossible or, at best, delayed. Moreover, such a phenomenon may also cause a risk of contamination or of siphoning effect, i.e. uncontrolled delivery of drug due to difference of height between the drug delivery device and the catheter, which are both linked with the IV line.

In some cases, the user will not even notice that the collar has cracked and is therefore weakened. Such a situation is particularly problematic when the connector is connected for example to a syringe operated by an automatic pump, like for the delivery of anaesthetic product during an operation. The pump is simply a machine which is not capable of noticing that the collar is cracked or broken and that inadequate injection occurs.

One aspect of the present invention is to provide an adaptor having a collar engageable with the end-piece of a drug delivery device, with very limited risks that the collar breaks at the time a connector is screwed thereon, regardless of the variation of intensity of the force that may be applied by a user for completing the screwing connection step.

A further aspect of the invention is a drug delivery device provided with such an adaptor, said adaptor being engaged or not with the end-piece of the drug delivery device.

An aspect of the invention is an adaptor for, or intended to be used with, a drug delivery device having a reservoir for containing a product, the reservoir having a distally projecting end-piece defining a passageway for the transfer of the product from the reservoir, said adaptor comprising:

- a collar engageable with said end-piece,
- adaptor securing means for limiting translational movement of said collar with respect to said end-piece once said collar is engaged with the end-piece,
- adaptor anti-rotation means for limiting the rotation of said collar with respect to said end-piece once said collar is engaged with the end-piece,
- deactivating means for neutralizing said adaptor anti-rotation means in response to a turning torque equal or greater than a predetermined value applied to said collar when said collar is engaged with said end-piece, thereby allowing the rotation of said collar with respect to said end-piece.

Another aspect of the present invention is a drug delivery device comprising:

- a reservoir for containing a product, said reservoir having a distally projecting end-piece defining a passageway for the transfer of the product from the reservoir,
- an adaptor, such as the adaptor above, having a collar engageable around said end-piece,
- securing means for limiting translational movement of said collar with respect to said end-piece once said collar is engaged with said end-piece,
- anti-rotation means for limiting the rotation of said collar with respect to said end-piece once said collar is engaged around said end-piece,
- deactivating means for neutralizing said anti-rotation means in response to a turning torque equal or greater than a predetermined value applied to said collar when said collar is engaged with said end-piece, thereby allowing the rotation of said collar with respect to said end-piece.

The distally projecting end-piece may have a longitudinal axis. The securing means may in particular block the movement of the collar in the distal direction with respect to the end-piece when the collar is engaged with the end-piece. The anti-rotation means may in particular prevent the rotation of the collar with respect to said end-piece around said longitudinal axis A under the effect of a turning torque applied to said collar once said collar is engaged with said end-piece.

In the present invention, once the collar of the adaptor is engaged with the end-piece of the drug delivery device, a connector may be screwed within a thread that may be present on an inner wall of the collar with no risk that the collar breaks or even cracks. Indeed, when a user, who handles the reservoir with one hand and the connector with the other hand, begins screwing the connector in the collar of the adaptor, the collar is maintained immobile with respect to the end-piece thanks to the anti-rotation means blocking or at least limiting the rotation of the collar around the longitudinal axis of the end-piece. As long as the connector has not reached the proximal end of the thread present on the collar, the user feels low resistance from the collar and he does not have to apply a high turning torque to the connector in order to screw it on the collar.

Thanks to the structure of the adaptor of the invention, the user is alerted when the connector has reached the proximal end of the thread present on the collar, for example by a signal, such as a sound signal, or a click, as will appear from the description below. Hence, on one hand, risks of carrying on the screwing too far and causing the collar to break or crack are avoided, and on the other hand, the end user can easily check that the connector is assembled correctly and safely fasten.

Indeed, in the adaptor and drug delivery device of the invention, when the connector reaches the proximal end of the thread of the collar, the user feels a resistance from the collar and the turning torque the user applies on the connector now tends to cause the collar to rotate. In devices of the prior art where the collar is permanently fixed to the end-piece with no possibility of rotating with respect to this end-piece, the result is that the collar breaks or cracks under the effect of the high turning torque applied by the user via the connector.

On the contrary, with the adaptor of the invention engageable with the end-piece of the drug delivery device of the invention, the deactivating means neutralize the anti-rotation means once the user reaches a predetermined value for the turning torque, i.e. the value corresponding to the opposition force felt by the user when the connector is safely threaded. The fact that the collar is then allowed to rotate with respect to the end-piece when the user applies a turning torque above said predetermined value prevents the collar from breaking or cracking. Moreover, when the user sees that the collar of the adaptor rotates with respect to the end-piece, he is alerted that the connector is safely and correctly connected to the collar and that transfer of the product from the reservoir to the IV via the connector may now be performed with no risk.

Part of the anti-rotation means may be located on the adaptor: they are referred to herein as adaptor anti-rotation means. Part of the anti-rotation means may be located on the end-piece of the drug delivery device: they are referred to herein as end-piece anti-rotation means. The adaptor anti-rotation means and the end-piece anti-rotation means may cooperate with each other so as to form the anti-rotation means.

In embodiments, said adaptor anti-rotation means comprises a part located on said collar and capable of being engaged in a complementary part located on an outer wall of said end-piece until said predetermined value of said turning torque is applied to said collar, when said collar is engaged with said end-piece. The complementary part may form the end-piece anti-rotation means.

In embodiments, said anti-rotation means comprises at least a part, located on said collar and at least a complementary part, located on an outer wall of said end-piece, said part and complementary part being engaged with each other until said predetermined value of said turning torque is applied to said collar, when said collar is engaged with said end-piece. In such a situation, said part and said complementary part thereby prevent or at least limit the rotation of said collar with respect to said end-piece.

In embodiments, said deactivating means being capable of being engaged with end-piece anti-rotation means for a turning torque less than said predetermined value when said collar is engaged with said end-piece, said deactivating means is radially outwardly deflectable under the effect of a turning torque equal to or greater than said predetermined value applied to said collar, said deactivating means thereby disengaging from said end-piece anti-rotation means and allowing the collar to rotate with respect to said end-piece.

In embodiments, said deactivating means being engaged with part of said anti-rotation means, in particular the end-piece anti-rotation means, for a turning torque less than said predetermined value when said collar is engaged with said end-piece, said deactivating means is radially outwardly deflectable under the effect of a turning torque equal to or greater than said predetermined value applied to said collar, said deactivating means thereby disengaging from said part of anti-rotation means and allowing the collar to rotate with respect to said end-piece.

In embodiments, said deactivating means comprises at least one skirt piece of said collar, and said end-piece anti-rotation means or part of anti-rotation means mentioned above comprising at least one projection located on an outer wall of said end-piece, said skirt piece and said projection being releasably engageable with each other when said collar is engaged with said end-piece and until said predetermined value of said turning torque is applied to said collar, said skirt piece radially outwardly deflecting and overcoming said projection when said turning torque is equal or greater than said predetermined value.

In embodiments, said skirt piece being provided with at least a radial wall, said projection is in abutment against said radial wall so as to limit, in cases so as to prevent, the rotation of said collar with respect to said end-piece when said collar is engaged with said end-piece and until said predetermined value of said turning torque is applied to said collar, said radial wall overcoming said projection under the effect of the radial outward deflection of said skirt piece when said turning torque is equal or greater than said predetermined value.

In embodiments, a plurality of longitudinal ridges is further defined on an inner wall of said skirt piece, each longitudinal ridge being releasably engageable with said projection so as to limit, in cases so as to prevent, the rotation of said collar with respect to said end-piece when said collar is engaged with said end-piece and until said predetermined value of said turning torque is applied to said collar, and so as to allow the rotation of said collar with respect to said end-piece when said turning torque is equal to or greater than said predetermined value.

In embodiments, a plurality of projections being defined on and spaced around an outer wall of said end-piece, said collar is provided with a plurality of skirt pieces spaced around the circumference of said collar to coincide with the spacing of said projections. For example, the outer wall of the end-piece may be provided with four projections regularly spaced around the circumference of the end-piece, and the collar may be provided with four skirt pieces regularly spaced around the circumference of the collar.

In the adaptor and drug delivery device of the invention, part of the securing means may be located on the adaptor: they are referred to herein as adaptor securing means. Part of the securing means may be located on the end-piece: they are referred to herein as end-piece securing means. The adaptor securing means and the end-piece securing means may cooperate with each other so as to form the securing means. In embodiments, an annular ridge being provided on an outer wall of the end-piece, said adaptor securing means comprise an abutment surface provided on the inner wall of the collar, said abutment surface coming in engagement onto said annular ridge when said collar is urged in the distal direction once it is engaged with said end-piece.

In embodiments, said securing means comprises an annular ridge provided on the outer wall of the end-piece and an abutment surface provided on the inner wall of the collar, said abutment surface coming in engagement onto said annular ridge when said collar is moved in the distal direction once it is engaged around said end-piece.

In embodiments, said abutment surface is an annular rim provided on the inner wall of said skirt piece(s). In embodiments, said abutment surface is formed of the distal ends of said longitudinal ridges.

In embodiments, said collar has a thread defined on an inner surface of a distal wall. As will appear from the description below, this thread is intended to cooperate with the complementary thread of a connector intended to be connected to said collar.

In embodiments, said distal wall of said collar is formed from a material selected from olefins, polyamide, polycarbonate, polyetherketone and combinations thereof. The olefins may be selected from polyolefins or cyclo-olefins, such as cyclo-olefin polymers and cyclo-olefin copolymers. Such a material ensures a good rigidity for the distal wall of the collar, where the thread is present and where the screwing of the connector will take place. Alternatively or in combination, the adaptor may further comprise reinforcing means defined on an outer surface of a distal wall of said collar. The reinforcing means may be additional outer ridges of material added on the outer surface of the distal wall of the collar.

In embodiments, said deactivating means are made of a material selected from olefins, polyamide, polycarbonate, thermoplastic elastomer, polyoxymethylene, polybutylene terephthalate, styrenic polymers, polyvinyl chloride, acrylonitrile butadiene styrene and combinations thereof. The olefins may be selected from polyolefins or cyclo-olefins, such as cyclo-olefin polymers and cyclo-olefin copolymers.

In embodiments, said end-piece is made of glass.

In other embodiments, said end-piece is made of plastic.

In embodiments, the adaptor may further comprise adaptor guiding means for ensuring the alignment of said collar on said end-piece when said collar is being engaged with the end-piece. In particular, the adaptor guiding means may ensure the alignment of said collar on the longitudinal axis of the end-piece in cooperation with end-piece guiding means located on the end-piece, said adaptor guiding means and end-piece guiding means forming altogether guiding means of the drug delivery device.

In embodiments, said radial wall(s) of said skirt piece(s) form at least part of said adaptor guiding means. Said adaptor guiding means may further comprise longitudinal grooves formed by the interspaces present between the longitudinal ridges.

In embodiments, the drug delivery device further comprises guiding means for ensuring the alignment of said collar on said end-piece, in particular on the longitudinal axis of said end-piece, when said collar is being engaged with said end-piece.

Said guiding means may comprise said projection(s), in particular as end-piece guiding means, and said radial wall (s) of said skirt piece(s), said projection(s) sliding along said radial wall(s) when said collar is being engaged with said end-piece. Said guiding means my further comprise longitudinal grooves defined by the interspaces present between the longitudinal ridges, each of said projection(s) engaging within one of said longitudinal grooves when said collar is being engaged with said end-piece.

In embodiments, said guiding means further comprise beveled surfaces of said longitudinal ridges, said beveled surfaces urging said projections in said longitudinal grooves when said collar is being engaged with said end-piece.

Another aspect of the invention is a drug delivery device comprising a reservoir for containing a product, said reservoir having a distally projecting end-piece as described above and defining a passageway for the transfer of the product from the reservoir, and an adaptor as described above engageable with said end-piece. Another aspect of the invention is an assembly comprising a drug delivery device as described above and an adaptor as described above engageable with the end-piece of said drug delivery device.

Figure 2:
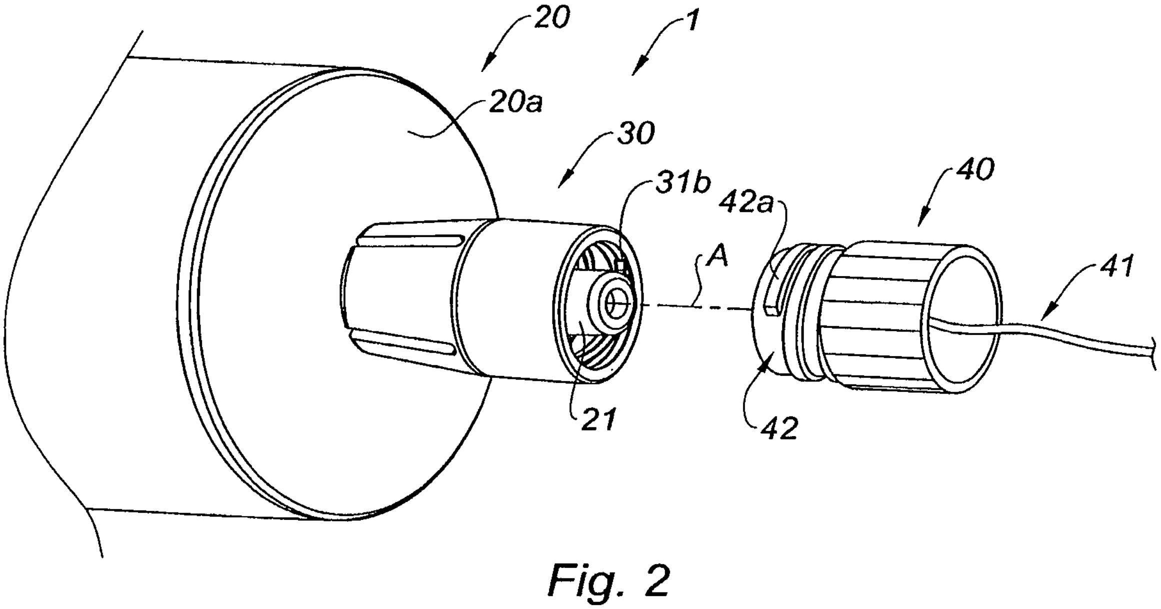
Figure 3:
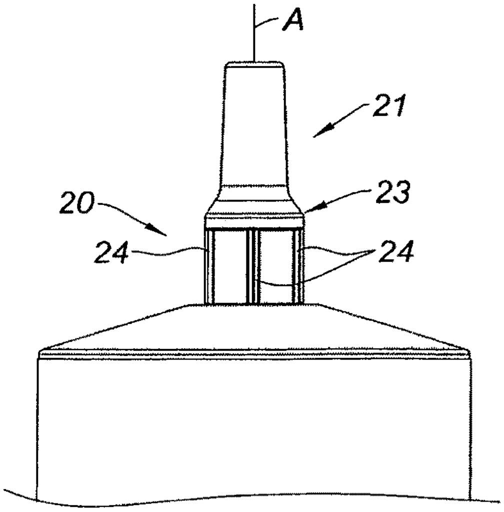
Figure 4:
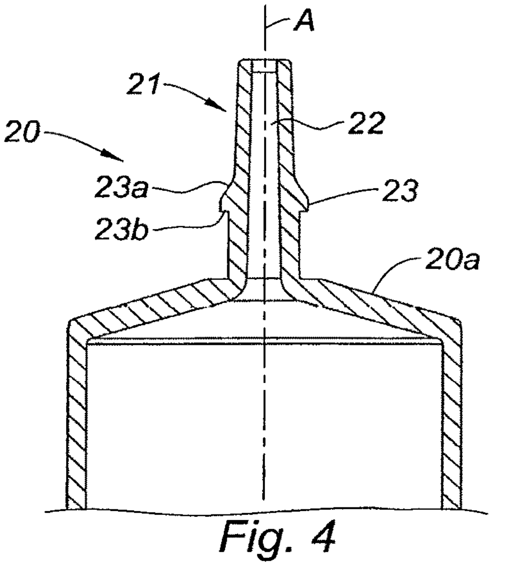
Figure 5:
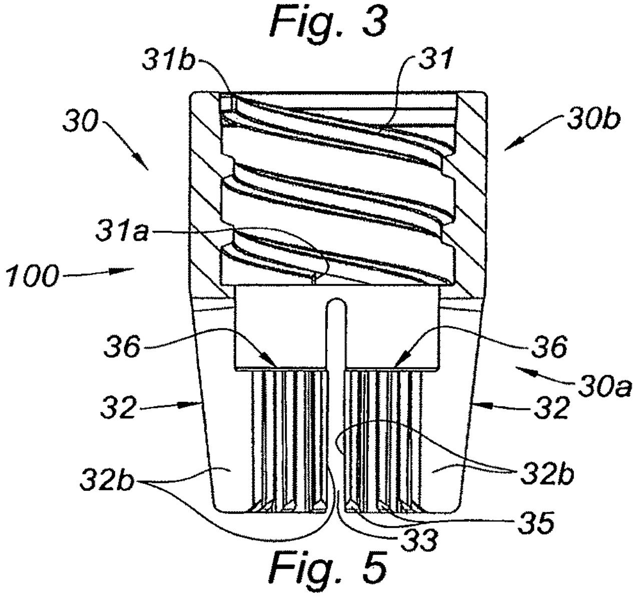
Figure 6:
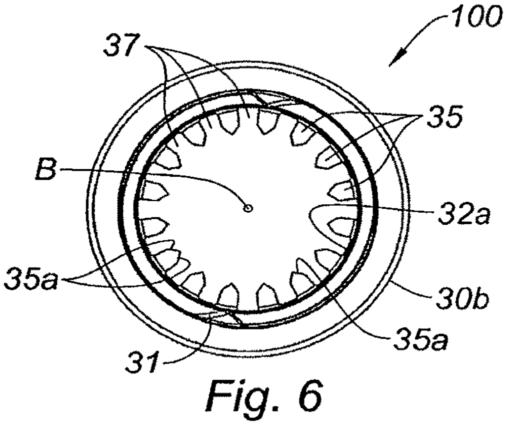
Figure 7:
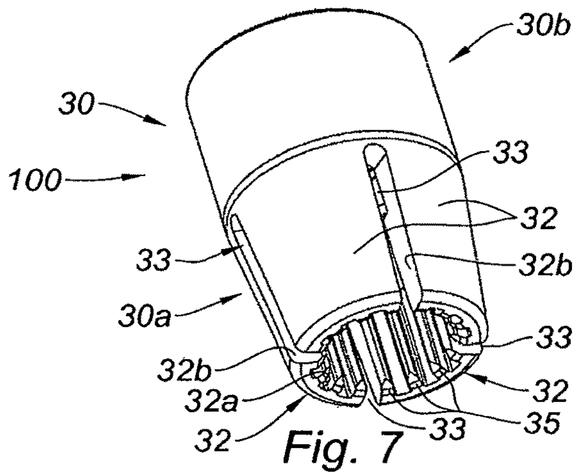
Figure 8:
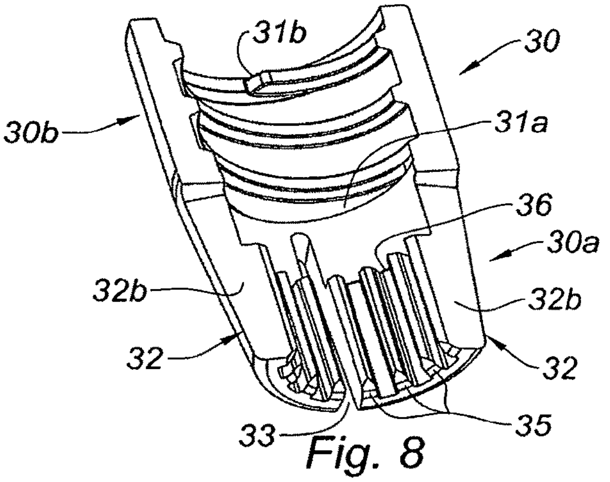
Figure 9:
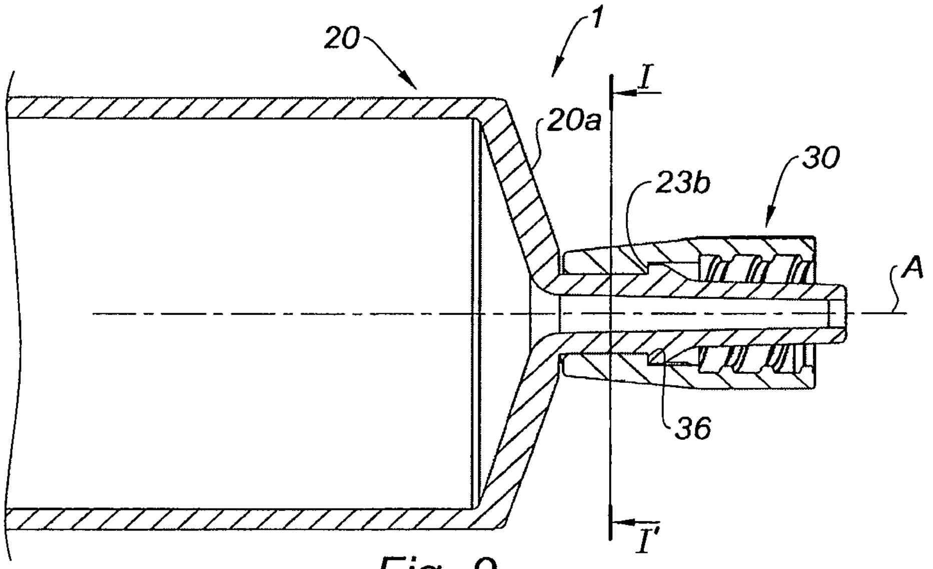
Figure 10:
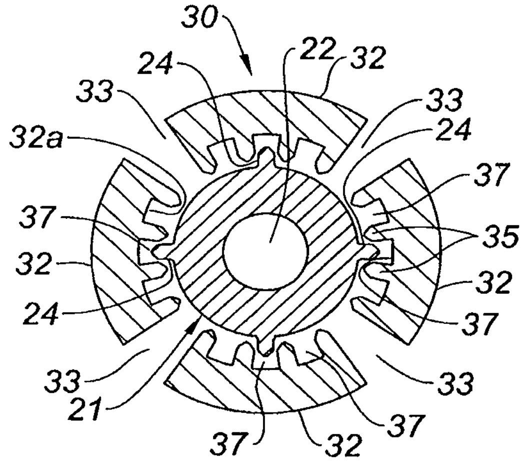
Figure 11:
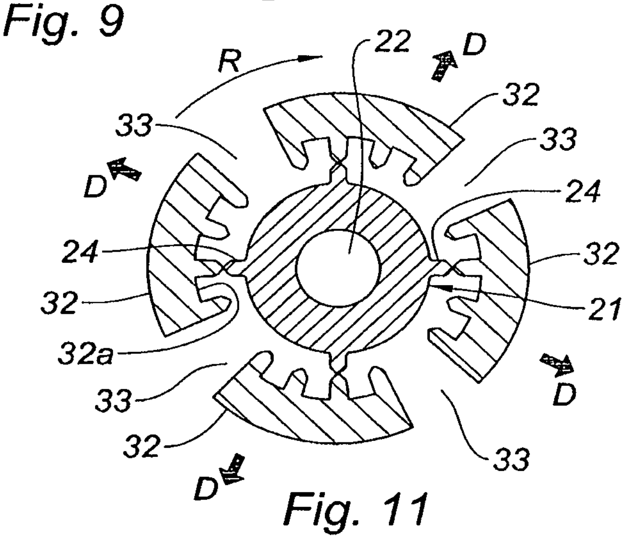
Figure 12:
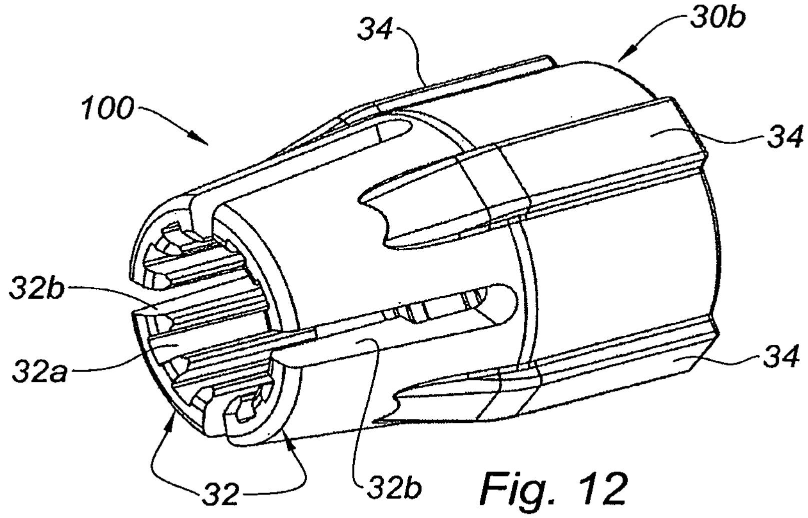
Figure 13:
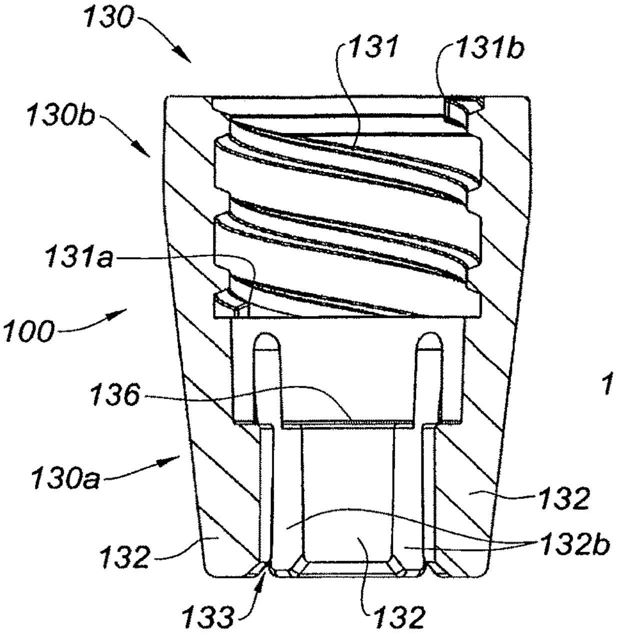
Figure 14:
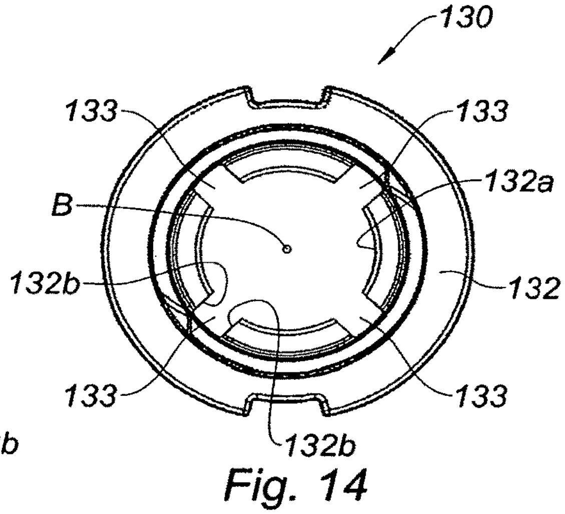
Figure 15:
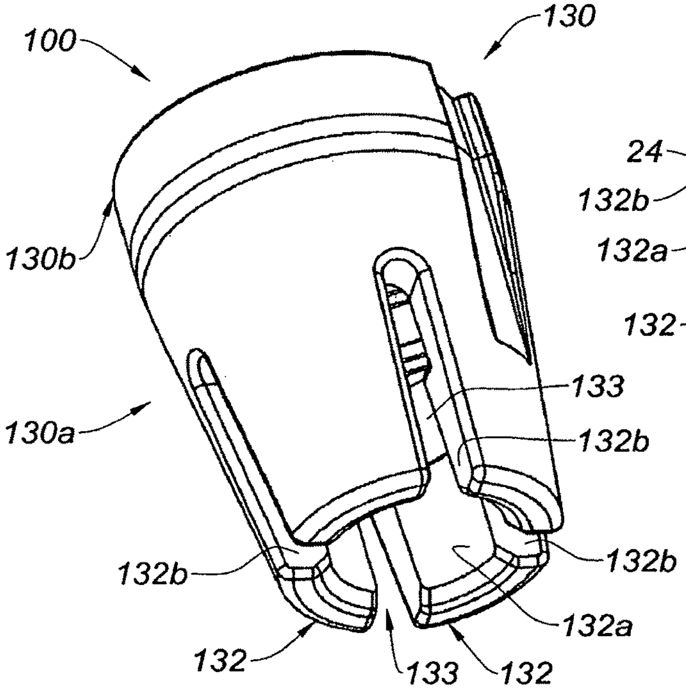
Figure 16:
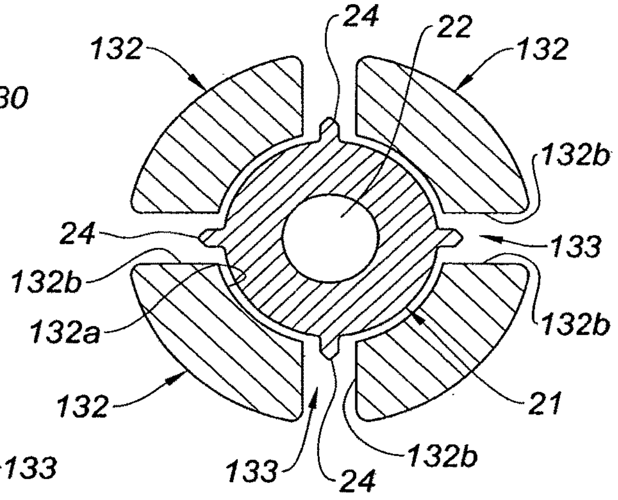

The adaptor and drug delivery device of the invention will now be further described in reference to the following description and attached drawings in which:

FIG. 1 is a perspective view of a first embodiment of the adaptor and drug delivery device of the invention, before engagement of the adaptor with the end-piece, FIG. 2 is a perspective view of the device of FIG. 1 once the collar of the adaptor is engaged on the end-piece of the reservoir, FIG. 3 is a partial side view of the reservoir of the drug delivery device of FIG. 1, FIG. 4 is a partial cross section view of the reservoir of FIG. 3, FIG. 5 is a cross section view of the adaptor of FIG. 1, FIG. 6 is a top view of the adaptor of FIG. 5, FIG. 7 is another perspective view of the adaptor of FIG. 1, FIG. 8 is a cross section view of the perspective view of FIG. 7, FIG. 9 is a cross section view of the drug delivery device of FIG. 2 with the adaptor engaged therewith, FIG. 10 is a cross section view along plane II' of FIG. 9, FIG. 11 is a cross section view of the drug delivery device of FIG. 10 once a turning torque has been applied on the collar, FIG. 12 is a perspective view of a second embodiment of the adaptor of the invention, FIG. 13 is a cross section view of another embodiment of the adaptor of the invention, FIG. 14 is a top view of adaptor of FIG. 13, FIG. 15 is a perspective view of adaptor of FIG. 13, FIG. 16 is a cross section view of the adaptor of FIG. 13 engaged with the end-piece of the drug delivery device of FIG. 1-12.

With reference to FIG. 1 are shown a drug delivery device 1 and an adaptor 100 according to the invention, the drug delivery device 1 comprising a reservoir 20 (partially shown) and the adaptor 100 comprising a collar 30.

The reservoir 20 is intended to receive a product, preferably a fluid like a liquid medicine, intended to be injected to a patient. The reservoir 20 has therefore the general shape of a container: for example, the reservoir may be a vial or a syringe body. The reservoir 20 is provided with an end-piece 21 projecting distally from a distal wall 20*a* of the reservoir 20. The end-piece 21 has a longitudinal axis A and defines a channel 22 providing a passageway for the transfer of the product from the reservoir 20.

The end-piece 21 may be made of any material usually used for manufacturing medical containers such as vials or syringes. For example, the end-piece 21 may be made of glass, in particular when the reservoir is a glass syringe. Alternatively, the end-piece may be made of plastic material. The end-piece and the walls of the reservoir may be of different materials.

With reference to FIGS. 1, 3 and 4, the end-piece 21 has the global shape of a portion of a hollow cone. The end-piece 21 is provided on its outer wall with an annular ridge 23, located substantially in a middle region of said end-piece 21. With reference to FIG. 4, the annular ridge 23 is provided with a slanted distal face 23*a* and with a radial proximal face 23*b*. The outer wall of the end-piece 21 is further provided with four longitudinal projections 24 regularly spaced around the circumference of the end-piece 21 and proximally spaced with respect to the annular ridge 23.

With reference to FIGS. 1 and 5-8, the collar 30 of the adaptor 100 will now be described with more details. As will be appear from the description below, the collar 30 is engageable around the end-piece 21. On the example shown, the collar 30 has a globally elongated shape and comprises a proximal region 30*a* and a distal region 30*b*.

The distal region 30*b* of the collar 30 has globally the shape of a tubular part and is provided on its inner wall with a thread 31, the function of which will be explained later. The thread 31 has a proximal end 31*a* and a distal end 31*b*. The distal region 30*b* of the collar 30 may be made of a material showing a certain rigidity. In an embodiment shown on FIG. 12, the outer wall of the distal region 30*b* is provided with reinforcing means under the form of outer ridges 34. Such outer ridges 34 enhances the rigidity of the distal region 30*b*. As will appear from the description below, the distal region 30*b* of the collar 30 is the one that is submitted to stress at the time a connector 40 (see FIG. 2) is connected to the adaptor 100: the material forming this distal region and the optional reinforcing means as described above confer a good rigidity to this distal region.

On the example shown on FIGS. 5 and 7, the proximal region 30*a* of the collar 30 comprises four skirt pieces 32 extending proximally from the proximal end of the distal region 30*b*. On the example shown, the four skirt pieces 32 are regularly spaced around the circumference of the collar 30 and they are separated from each other by four longitudinal slots 33. As will appear in the description below, the skirt pieces 32 are flexible and capable of being radially outwardly deflected under the effect of a outwardly radial force exerted on their inner wall 32*a*. Moreover, each skirt piece 32 has two lateral sides forming radial walls 32*b*.

In other embodiments not shown, the proximal region of the collar could comprise only one skirt, or alternatively two, three or five or more skirt pieces, as long as this skirt or these skirt pieces are radially outwardly deflectable.

As such, the skirt or skirt pieces 32 of the proximal region of the collar 30 may be made of any material having enough elasticity for allowing the skirt or skirt pieces to be deflectable as explained above. For example, such a material may be selected from olefins, such as polyolefins or cyclo-olefins, in particular cyclo-olefin polymers and cyclo-olefin copolymers, polyamide or nylon, polycarbonate, thermoplastic elastomer, polyoxymethylene, polybutylene terephthalate, styrenic polymers, polyvinyl chloride, acrylonitrile butadiene styrene, and combinations thereof.

With reference to FIGS. 7 and 8, each skirt piece 32 is provided on its inner wall 32*a* with a plurality of substantially parallel longitudinal ridges 35. The distal ends of these longitudinal ridges 35 form together an abutment surface 36.

With reference to FIG. 6, the plurality of longitudinal ridges 35 defines a plurality of longitudinal grooves 37 located therebetween. Moreover, each longitudinal ridge 35 is provided with beveled surfaces 35*a* in the direction of the longitudinal axis B of the collar 30.

As will appear from the description below, the adaptor 100 of the invention is particularly useful for connecting a connector to the end-piece 21 of the drug delivery device 1 with very limited risk of damaging the collar 30. Anyway, previously to connecting a connector to the drug delivery device 1, the user must engage the collar 30 on the end-piece 21. The engagement of the collar 30 of the adaptor 100 of the invention on the end-piece 21 of the drug delivery device 1 of the invention will now be described with reference to FIGS. 1, 2 and 9.

Usually, the user is provided with the drug delivery device 1 and the adaptor 100 before engagement of the collar 30 on the end-piece 21 as shown on FIG. 1. The user then grasps the reservoir 20 in one hand and the collar 30 in the other hand and approaches the proximal region 30*a* towards the distal end of the end-piece 21 along the direction of the longitudinal axis A. The inner wall 32*a* of the skirt pieces 32 of the proximal region 30*a* of the collar 30 slides along the outer wall of the end-piece 21 until it reaches the slanted face 23*a* of the annular ridge 23 of the end-piece 21. Thanks to the capability of the skirt pieces 32 to be radially and outwardly deflected, the skirt pieces 32 deflect in the outward direction, overcome the annular ridge 23 and come back to their rest state, in which they face the longitudinal projections 24 of the proximal region of the end-piece 21.

In this position, as shown on FIGS. 2 and 9, the collar 30, and thus the adaptor 100, is securely engaged on the end-piece 21. The collar 30, and thus the adaptor 100, is blocked, or at least limited, in translation with respect to the longitudinal axis A both in the proximal direction, by virtue of the proximal end of the collar 30 coming in abutment against the distal wall 20*a* of the reservoir 20, and in the distal direction, by virtue of the abutment surface 36 coming in contact with the radial proximal face 23*b* of the annular ridge 23 of the end-piece 21. As such, the abutment surface 36 and the radial proximal face 23*b* of the annular ridge 23 form securing means for blocking or at least limiting translational movement of the collar 30, in particular in the distal direction, with respect to the end-piece 21 when said collar 30 is engaged with said end-piece 21. The abutment surface 36 forms adaptor securing means whereas the radial proximal face 23*b* of the annular ridge 23 forms end-piece securing means.

Moreover, in the position of the drug delivery device 1 shown on FIGS. 2 and 9, wherein the collar 30 is engaged with the end-piece 21, and in the absence of a significant turning torque applied on the collar 30 as will be described later, the collar 30, and thus the adaptor 100, is further blocked or at least limited in rotation with respect to the end-piece 21, by virtue of the longitudinal projections 24 engaged in the longitudinal grooves 37 or in the longitudinal slots 33 as shown on FIG. 10. Indeed, during the step of engaging the collar 30 on the end-piece 21, the longitudinal projections 24 of the end-piece 21 come in contact with the longitudinal ridges 35 of the skirt pieces 32 or with the radial walls 32*b* of the skirt pieces 32: during the proximal movement of the collar 30 with respect to the end-piece 21, the beveled surfaces 35*a* of the longitudinal ridges 35 force the longitudinal projections 24 towards the longitudinal grooves 37 and/or the radial walls 32*b* of the skirt pieces 32 come in contact with the longitudinal projections 24, forcing these longitudinal projections 24 into the slots 33: the beveled surfaces 35*a* and/or the radial walls 32*b* of the skirt pieces 32 act as adaptor guiding means for correctly aligning the collar 30 on the end-piece 21 along the longitudinal axis A. The longitudinal projections 24 act as end-piece guiding means. The longitudinal projections 24 and the beveled surfaces 35*a* and/or the radial walls 32*b* of the skirt pieces 32 act altogether as guiding means for ensuring the alignment of the collar 30 on the end piece when the collar is being engaged with the end-piece 21.

Moreover, the longitudinal projections 24 on one hand, and the radial walls 32*b* and longitudinal ridges 35 on the other hand, act also as anti-rotation means for preventing the rotation of the collar 30 with respect to the end-piece 21 around the longitudinal axis A under the effect of a turning torque applied to said collar 30. The longitudinal projections 24 act as end-piece anti-rotation means and the radial walls 32*b* and longitudinal ridges 35 act as adaptor anti-rotation means.

The adaptor 100 of the invention nevertheless allows the deactivation of such anti-rotation means once the turning torque applied to the collar 30 reaches a predetermined value likely to cause the collar 30 to break or crack under the force it is submitted to when a connector is screwed thereon.

The behavior of the collar 30 of the adaptor 100 of the invention, once engaged with the end-piece 21 and when a connector is screwed therein will now be described with reference to FIGS. 2 and 9-11.

With reference to FIG. 2 is shown the drug delivery device 1 of the invention, with the collar 30 of the adaptor 100 engaged with the end-piece 21, and a connector 40 intended to be connected to the end-piece 21 of the drug delivery device 1.

As explained above, the handling of liquid medicine for a parenteral administration to a patient which is carried out via a perfusion device, as often in hospitals or in emergency situations, implies the use IV lines which need to be connected to drug delivery devices. With reference to FIG. 2, the connector 40 comprises an IV line 41, the distal end (not shown) of which is connected to the vein of a patient (not shown). The connector 40 is provided at its proximal end with a thread 42 intended to cooperate with the thread 31 of the collar 30 so as to safely connect the connector 40 to the drug delivery device 1, and by consequence to safely connect the IV line 41 to the end-piece 21, thereby enabling the transfer of the product from the reservoir 20 to the vein of the patient.

During the treatment of a patient, or during an operation if the product is an anaesthetic product, the product must be delivered to the patient on a continuous basis and, once the reservoir of a drug delivery device is emptied, another drug delivery device 1 with a filled reservoir must be connected to the IV line 41 via the connector 40.

For proceeding to this connecting step, the user grasp in one hand the drug delivery device 1 with the collar 30 of the adaptor 100 engaged with the end-piece 21 as shown on FIG. 2 and in the other hand the connector 40. The user approaches the proximal end 42*a* of the thread 42 of the connector 40 to the distal end 31*b* of the thread 31 of the collar 30 and he begins to screw the connector 40 within the collar 30.

During this screwing step, as long as the connector 40 is not fully screwed on the collar 30, the turning torque applied by the user on the connector 40 and incidentally on the collar 30 by the action of screwing the connector 40 thereon is low and the longitudinal projections 24 of the end-piece 21 cooperate with the longitudinal ridges 35 of the skirt pieces 32 of the collar 30 in order to act as anti-rotation means and to prevent the rotation of the collar 30 with respect to the end-piece 21, as shown on FIG. 10. The screwing is therefore rendered easy.

The turning torque applied by the user on the connector 40 in view of screwing it to the collar 30 is transferred to the collar when the connector 40 is fully screwed to the collar 30: this may happen for example either when the proximal end 42*a* of the thread 42 of the connector 40 comes in abutment with the proximal end 31*a* of the thread 31 of the collar 30, or when a proximal surface of the connector 40 comes in abutment with a distal surface of the collar 30, or when sufficient friction forces between the thread 42 of the connector 40 and the thread 31 of the collar 30 are formed. When the turning torque thus transferred to the collar 30 reaches a predetermined value, the collar 30 is urged to rotate with respect to the end-piece 21.

In devices of the prior art, where the collar is for example permanently fixed with respect to the end-piece, the collar can not absorb this additional turning torque and it is caused to crack or break.

On the contrary, in the drug delivery device 1 and adaptor 100 of the invention, when the turning torque transferred onto the collar 30 reaches a predetermined value, for example a value of 50 N·cm, the flexible skirt pieces 32 are caused to deflect radially outwardly and therefore act as deactivating means of the anti-rotation means, thereby enabling the collar 30 to rotate and preventing said collar 30 from cracking and/or breaking.

With reference to FIG. 10, as long as the turning torque transferred onto the collar 30 as explained above is less than a predetermined value, the longitudinal projections 24 are engaged in the longitudinal grooves 37 defined by the longitudinal ridges 35 of the flexible skirt pieces 32 and are in abutment against the beveled surfaces 35*a* of said longitudinal ridges 35.

With reference to FIG. 11, when the turning torque, shown as R on the Figure, transferred to the collar 30 is equal or greater than a predetermined value, the longitudinal projections 24 slide on the beveled surfaces 35*a* and cause the skirt pieces 32 to deflect radially outwardly in the direction of the arrows referenced D on the FIG. 11. The longitudinal projections 24 are allowed to overcome the longitudinal ridges 35 and they get engaged in the adjacent longitudinal groove 37, thereby maintaining the correct axial alignment of the collar 30 on the end-piece 21.

The deflection of the skirt pieces 32 not only avoid the breaking and/or cracking of the collar 30 but it also informs the user on the fact that the connector 40 is fully screwed within the collar 30 and that the IV line 41 is safely connected to end-piece 21 of the drug delivery device 1. For example, the user may be alerted by a click or the sound produced by a projection 24 when it comes in abutment with the adjacent longitudinal ridge 35 after it has overcome the previous longitudinal ridge 35.

With reference to FIGS. 13-16 is shown another embodiment of the adaptor 100 of the invention for which the collar 130 is provided with four flexible skirt pieces 132 free of longitudinal ridges on their inner walls 132*a*. The collar 130 of FIGS. 13-16 may be used with the same delivery device 1 and end-piece 21 of that of FIGS. 1-11. In such an embodiment of the adaptor 100, the adaptor anti-rotation means comprise the radial walls 132*a* formed by the lateral sides of the skirt pieces 132.

As shown on FIGS. 14 and 15, the four skirt pieces 132 are spaced around the longitudinal axis B of the collar 130 and they are separated from each other by longitudinal slots 133. When the collar 130 is engaged with the end-piece 21 of the drug delivery device 1 as shown on FIG. 16, the projections 24 of the end-piece 21 are forced in the longitudinal slots 133 by the radial walls 132*b* acting as adaptor guiding means. Once the collar 130 is engaged with the end-piece 21, the projections 24 are in abutment against the radial walls 132*b* as long as the turning torque applied on the collar 130 is less than the predetermined value as defined above. The radial wall 132*b* form adaptor anti-rotation means.

Since the skirt pieces 132 are radially outwardly deflectable, when a turning torque equal to or greater than said pretermined value is applied on said collar 130, the skirt pieces 132 deflect radially outwardly and they overcome the resistance of the projections 24, thereby allowing the rotation of the collar 130 with respect to the end-piece 21, as described before for the embodiment of FIGS. 1-11.

Like the embodiment of FIGS. 1-11, the collar 130 of FIGS. 13-16 is provided with an annular rim 136 intended to be in abutment against the proximal face 23*b* of the annular ridge 23 of the end-piece when the collar 130 is engaged with the end-piece 21.

The predetermined value as described above for the turning torque is function of the size and structure of the collar and of the materials forming the collar, in particular its flexible elements, and the end-piece.

For example, for an end-piece made of a thermoplastic material selected from olefins, in particular polyolefins and cyclo-olefins, for example cyclo-olefin polymers and cyclo-olefin copolymers, polyamide or nylon, polycarbonate and combinations thereof and a collar as described in FIGS. 1-11 for which the skirt pieces are made of a thermoplastic material selected from olefins, polyamide, polycarbonate, thermoplastic elastomer, polyoxymethylene, polybutylene terephthalate, styrenic polymers, polyvinyl chloride, acrylonitrile butadiene styrene, and combinations thereof, the predetermined value for the turning torque is: 50 N·cm.

The adaptor and drug delivery device of the invention allow the safe connection of an IV line connector to the end-piece of said device with no risk that the collar of said device be broken or cracked, regardless of the force applied on the connector in order to connect it to the device.

What is claimed is:

1. An adaptor for use with a drug delivery device having a reservoir for containing a product, said adaptor comprising:

a collar engageable with a distally projecting end-piece of said reservoir, said collar comprising an abutment surface on an inner wall of the collar, wherein said abutment surface is configured to limit translational movement of said collar with respect to said distally projecting end-piece once said collar is engaged with the distally projecting end-piece;

at least one adaptor anti-rotation member comprising a part located on said collar and capable of being engaged in a complementary part located on an outer wall of said distally projecting end-piece until a predetermined value of turning torque is applied to said collar, when said collar is engaged with said distally projecting end-piece; and at least one deactivating member configured to neutralize said at least one adaptor anti-rotation member in response to a turning torque equal to or greater than a predetermined value applied to said collar when said collar is engaged with said distally projecting end-piece, thereby allowing the rotation of said collar with respect to said distally projecting end-piece.

2. The adaptor according to claim 1, wherein the inner wall of said collar is provided with at least one ridge having a distal end; and wherein the distal end of the at least one ridge forms the abutment surface.

3. The adaptor according to claim 2, wherein the at least one ridge is a plurality of ridges; and wherein the distal ends of the plurality of ridges together form the abutment surface.

4. The adaptor according to claim 2, wherein the at least one ridge extends longitudinally along the inner wall parallel to a central axis of the collar.

5. The adaptor according to claim 4, wherein the at least one ridge is a plurality of ridges; and wherein the distal ends of the plurality of ridges together form the abutment surface.

6. The adaptor according to claim 1, wherein said collar has a globally elongated shape and comprises a distal region and an opposite, proximal region; and wherein said abutment surface is disposed between and spaced from said distal region and said proximal region.

7. The adaptor according to claim 6, wherein said distal region of said collar has globally the shape of a tubular part and is provided with a thread on an inner wall of said distal region.

8. The adaptor according to claim 1, wherein said abutment surface is an annular rim provided on the inner wall of a portion of said collar.

9. The adaptor according to claim 1, wherein said at least one deactivating member comprises at least one skirt piece, and wherein said at least one adaptor anti-rotation member comprises at least one projection located on the outer wall, said at least one skirt piece and said at least one projection being releasably engageable with each other when said collar is engaged with said distally projecting end-piece and until said predetermined value of said turning torque is applied to said collar.

10. The adaptor according to claim 1, wherein said at least one deactivating member is made of a material selected from olefins, polyamide, polycarbonate, thermoplastic elastomer, polyoxymethylene, polybutylene terephthalate, styrenic polymers, polyvinyl chloride, acrylonitrile butadiene styrene, and combinations thereof.

11. The adaptor according to claim 1, wherein at least a portion of said collar is formed from a material selected from olefins, polyamide, polycarbonate, polyetherketone, and combinations thereof.

12. The adaptor according to claim 1, further comprising at least one reinforcing member defined on an outer surface of said collar.

13. The adaptor according to claim 1, further comprising at least one adaptor guiding member ensuring the alignment of said collar on said distally projecting end-piece when said collar is being engaged with the distally projecting end-piece.

14. A drug delivery device comprising:

a reservoir for containing a product, said reservoir having a distally projecting end-piece defining a passageway for the transfer of the product from the reservoir; and an adaptor having a collar engageable with said distally projecting end-piece, wherein said abutment surface is configured to limit translational movement of said collar with respect to said distally projecting end-piece once said collar is engaged with the distally projecting end-piece;

at least one adaptor anti-rotation member comprising a part located on said collar and capable of being engaged in a complementary part located on an outer wall of said distally projecting end-piece until a predetermined value of turning torque is applied to said collar, when said collar is engaged with said distally projecting end-piece; and at least one deactivating member configured to neutralize said at least one adaptor anti-rotation member in response to a turning torque equal to or greater than a predetermined value applied to said collar when said collar is engaged with said distally projecting end-piece, thereby allowing the rotation of said collar with respect to said distally projecting end-piece.

15. The drug delivery device according to claim 14, wherein the inner wall of said collar is provided with at least one ridge having a distal end; and wherein the distal end of the at least one ridge forms the abutment surface.

16. The drug delivery device according to claim 15, wherein the at least one ridge is a plurality of ridges; and wherein the distal ends of the plurality of ridges together form the abutment surface.

17. The drug delivery device according to claim 15, wherein the at least one ridge extends longitudinally along the inner wall parallel to a central axis of the collar.

18. The drug delivery device according to claim 17, wherein the at least one ridge is a plurality of ridges; and wherein the distal ends of the plurality of ridges together form the abutment surface.

19. The drug delivery device according to claim 14, wherein said collar has a globally elongated shape and comprises a distal region and an opposite, proximal region; and wherein said abutment surface is disposed between and spaced from said distal region and said proximal region.

20. The drug delivery device according to claim 14, wherein said abutment surface is an annular rim provided on the inner wall of a portion of said collar.

* * * * *